United States Patent
Taylor

(10) Patent No.: US 6,685,705 B1
(45) Date of Patent: Feb. 3, 2004

(54) SIX-AXIS AND SEVEN-AXIS ADJUSTABLE CONNECTOR

(75) Inventor: Harold Sparr Taylor, Memphis, TN (US)

(73) Assignee: SDGI Holdings, Inc., Wilmington, DE (US)

(*) Notice: Subject to any disclaimer, the term of this patent is extended or adjusted under 35 U.S.C. 154(b) by 258 days.

(21) Appl. No.: 09/694,703

(22) Filed: Oct. 23, 2000

(51) Int. Cl.[7] .............................................. A61B 17/56
(52) U.S. Cl. .............................. 606/61; 606/72; 606/73
(58) Field of Search ............................. 606/53, 54, 61, 606/72, 73

(56) References Cited

U.S. PATENT DOCUMENTS

| | | |
|---|---|---|
| 2,439,995 A | 4/1948 | Thrailkill |
| 4,987,892 A | 1/1991 | Krag et al. |
| 5,002,542 A | 3/1991 | Frigg |
| 5,053,034 A | 10/1991 | Olerud |
| 5,129,900 A | 7/1992 | Asher et al. |
| 5,254,118 A | 10/1993 | Mirkovic |
| 5,306,275 A | 4/1994 | Bryan |
| 5,344,422 A | 9/1994 | Frigg |
| 5,352,226 A | 10/1994 | Lin |
| 5,380,323 A | 1/1995 | Howland |
| 5,498,262 A | 3/1996 | Bryan |
| 5,562,663 A | 10/1996 | Wisnewski et al. |
| 5,584,831 A | 12/1996 | McKay |
| 5,591,165 A | 1/1997 | Jackson |
| 5,613,968 A | 3/1997 | Lin |
| 5,643,260 A | 7/1997 | Doherty |
| 5,643,263 A | 7/1997 | Simonson |
| 5,643,264 A | 7/1997 | Sherman et al. |
| 5,645,544 A | 7/1997 | Tai et al. |
| 5,688,263 A | 11/1997 | Hauptmann et al. |
| 5,688,275 A | 11/1997 | Koros et al. |
| 5,709,685 A | 1/1998 | Dombrowski et al. |
| 5,741,255 A | 4/1998 | Krag et al. |
| 5,776,135 A * | 7/1998 | Errico et al. .................. 606/60 |
| 5,810,816 A | 9/1998 | Roussouly et al. |
| 5,879,351 A | 3/1999 | Viart |
| 5,885,285 A | 3/1999 | Simonson |
| 5,938,663 A | 8/1999 | Petreto |
| 5,947,965 A | 9/1999 | Bryan |
| 5,947,967 A | 9/1999 | Barker |
| 5,976,135 A * | 11/1999 | Sherman et al. ............... 606/61 |
| 5,984,928 A | 11/1999 | Hermann |
| 6,027,533 A | 2/2000 | Olerud |
| 6,030,388 A | 2/2000 | Yoshimi et al. |
| 6,063,089 A * | 5/2000 | Errico et al. .................. 606/60 |

(List continued on next page.)

FOREIGN PATENT DOCUMENTS

| | | | |
|---|---|---|---|
| EP | 0 553 424 A1 | 8/1993 | |
| EP | 0 786 235 A2 B1 | 7/1997 | |
| EP | 0 982 007 A2 | 3/2000 | ........... A61B/17/70 |
| EP | 0 982 007 A2 A3 | 3/2000 | ........... A61B/17/70 |
| FR | 2 692 471 A1 | 12/1993 | |
| FR | 2 697 743 A1 | 5/1994 | |
| FR | 2 806 902 A1 | 10/2001 | |
| WO | WO 01/67972 A2 A3 | 9/2001 | |

Primary Examiner—Rosiland K. Rollins
(74) Attorney, Agent, or Firm—Woodard, Emhardt, Moriarty, McNett & Henry LLP

(57) ABSTRACT

A connection assembly between a spinal implant rod and a vertebral anchor. The connection assembly includes a spindle and a housing. The spindle has an aperture for receiving a spinal implant rod in a spinal implant system. And structure for urging the rod within the aperture, such as a setscrew, is provided through a suitable threaded opening in the spindle so as to be extendable into the aperture. The housing has an aperture for receiving a shaft or shank of a vertebral anchor of a spinal implant system. The housing also has an aperture for receiving a generally cylindrical projection portion of the spindle. Structure for urging the shank of the vertebral anchor against the projection portion, such as a setscrew, is provided through a suitable threaded opening in the housing.

28 Claims, 5 Drawing Sheets

U.S. PATENT DOCUMENTS

| | | |
|---|---|---|
| 6,083,226 A | 7/2000 | Fiz |
| 6,086,588 A | 7/2000 | Ameil et al. |
| 6,106,526 A | 8/2000 | Harms et al. |
| 6,123,706 A | 9/2000 | Lange |
| 6,183,473 B1 | 2/2001 | Ashman |
| 6,187,005 B1 | 2/2001 | Brace et al. |
| 6,210,413 B1 * | 4/2001 | Justis et al. .................. 606/60 |
| 6,231,575 B1 * | 5/2001 | Krag .......................... 606/61 |
| 6,248,107 B1 | 6/2001 | Foley et al. |

* cited by examiner

SIX-AXIS AND SEVEN-AXIS ADJUSTABLE CONNECTOR

BACKGROUND OF THE INVENTION

Spinal implant systems provide a rod for supporting the spine and for properly positioning components of the spine for various treatment purposes. Bolts, screws, and hooks are typically secured to the vertebrae for connection to the supporting rod. These vertebral anchors must frequently be positioned at various angles due the anatomical structure of the patient, the physiological problem being treated, and the preference of the physician. It is difficult to provide secure connections between the spinal support rod and these vertebral anchors at all the various angles and elevations that are required, especially where there are different distances between the rod and bolts and where these components are located at different heights on the patient.

What is needed is a connection assembly between a spinal rod and a vertebral anchor that allows the surgeon to fix the desired elevation between a rod and the bone anchor as well as fix the desired angle between the anchor and rod. The following invention is one solution to that need.

SUMMARY OF THE INVENTION

In one aspect, this invention is a connection assembly between a spinal implant rod and a vertebral anchor. The connection assembly has a spindle. The spindle has an aperture for receiving a portion of a spinal implant rod and a compression member forceably, for example threadably, engageable into the spindle to urge a spinal implant rod against the internal walls of the aperture. The connection assembly also has housing, for example a spindle block. The housing has an aperture for receiving a portion that projects from the spindle and an aperture for receiving a portion of a vertebral anchor, the aperture for the spindle also being open to the aperture for the vertebral anchor. A second compression member is then forceably engaged into the housing to urge the spindle against the vertebral anchor (or the vertebral anchor against the spindle), securing the housing to the vertebral anchor and the spindle.

In another aspect this invention is a connection assembly between a spinal implant rod and a vertebral anchor. This connection assembly also has spindle and compression member as previous described. This embodiment uses a means for connecting the vertebral anchor to the spindle at a variable angle.

DETAILED DESCRIPTION OF THE PREFERRED EMBODIMENT

Specific language is used in the following description to publicly disclose the invention and to convey its principles to others. No limits on the breadth of the patent rights based simply on using specific language are intended. Also included are any alterations and modifications to the description that should normally occur to one of average skill in this technology.

Figure 1:
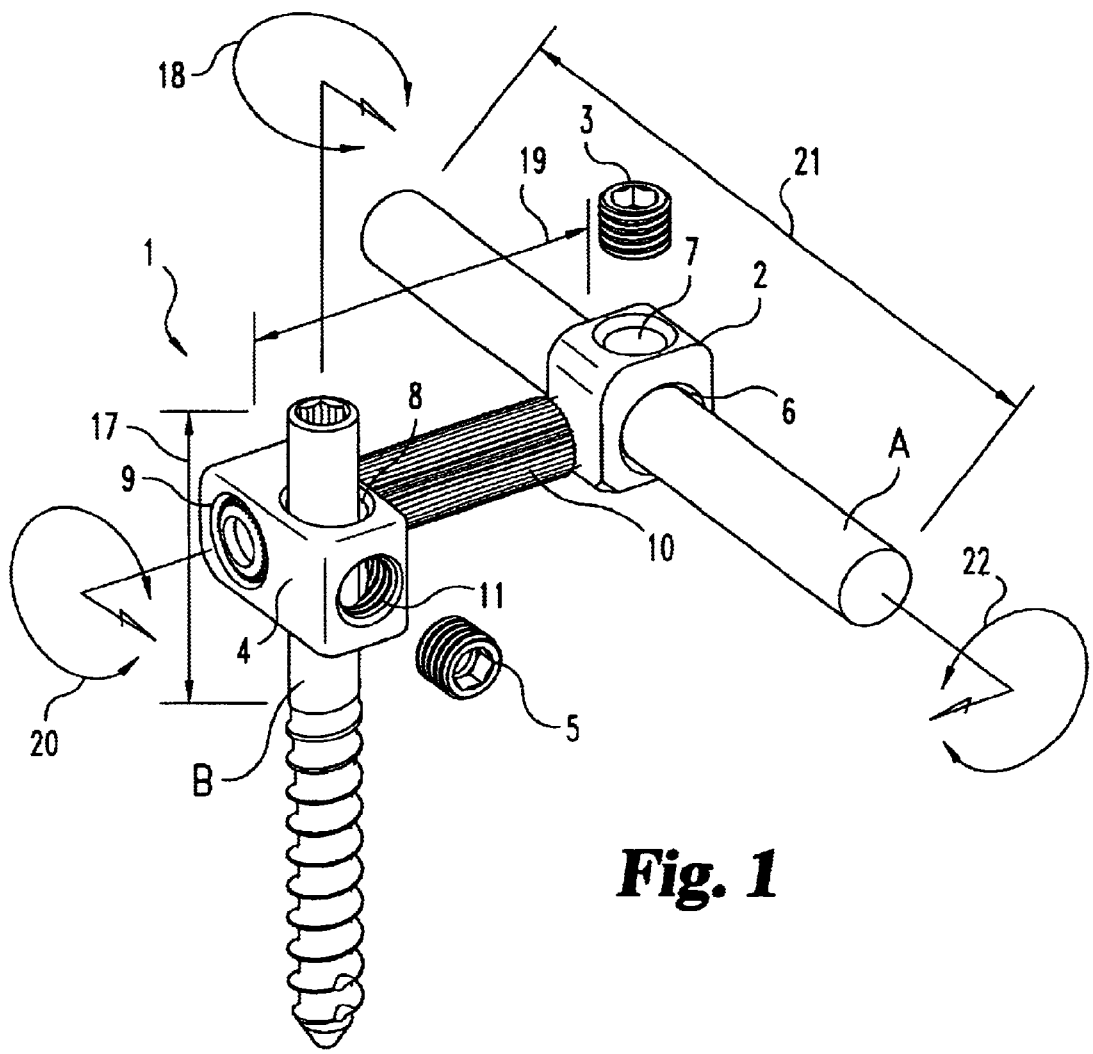
FIG. 1 is a perspective view of one embodiment of the present invention.

A connection assembly 1 according to one embodiment of the invention is shown in FIG. 1. Connection assembly 1 includes a spindle 2 and a housing or spindle block 4. Spindle 2 has an aperture 6 for receiving a rod "A" in a spinal implant system. While a closed aperture is shown, it will nevertheless be understood that an open-sided aperture may also be used to permit top-loading of the rod. And structure for urging the rod within aperture 6, such as the set screw 3, is provided through a suitable threaded opening 7 in spindle 2 so as to be extendable into aperture 6. The housing 4 has an aperture 8 for receiving a shaft or shank of a vertebral anchor "B" of a spinal implant system. Spindle block or housing 4 also has an aperture 9 for receiving a generally cylindrical projection portion 10 of spindle 2. While closed apertures 8 and 9 are shown, it will nevertheless be understood that either or both may also be open-sided. Structure for urging the shank of vertebral anchor "B" against the generally cylindrical projection portion, such as set screw 5, is provided through a suitable threaded opening 11 in housing 4 so as to be extendable into aperture 8 or 9.

Figure 3:
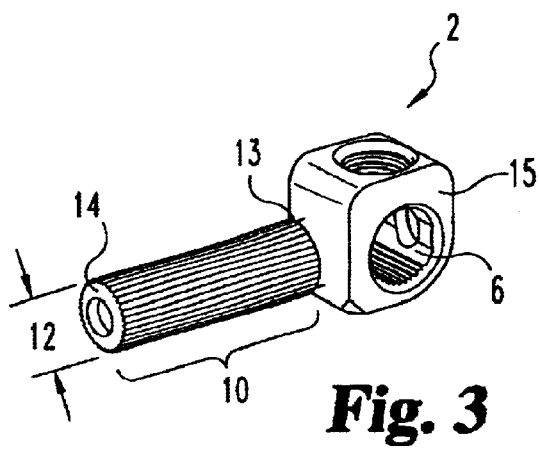
FIG. 3 is a perspective view of a spindle used in one embodiment of the present invention.
Figure 5:
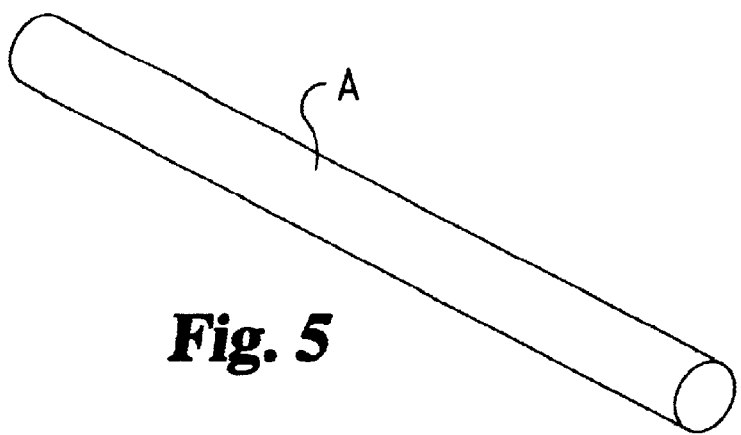
FIG. 5 is a perspective view of a spinal implant rod with which the present invention may be used.

Details of spindle 2 are shown in FIG. 3. Spindle 2 has a generally cylindrical projection portion 10. Projection portion 10 is of a substantially constant diameter 12 from a point 13 to end 14, and may be either hollow or solid. The opposite end 15 includes an aperture 6 for receiving a spinal implant rod "A" (FIG. 5). The length of projection portion 10 is preferably roughened or scored, as well as the internal walls of aperture 6. An example of such a spindle is commercially available as part of the LIBERTY™ system offered by Medtronic Sofamor Danek located in Memphis, Tenn., U.S.A. Spindle 2 is locked to rod "A" by tightly threading setscrew 3 inside aperture 7 and against rod "A".

Figure 2:
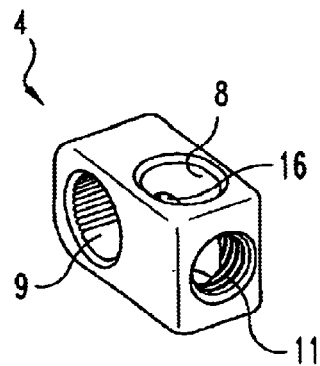
FIG. 2 is a perspective view of a housing used in one embodiment of the present invention.
Figure 4:
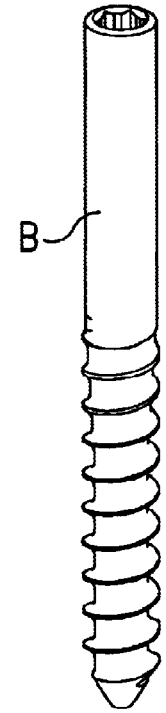
FIG. 4 is a perspective view of a vertebral anchor with which the present invention may be used.

Details of housing or spindle block 4 are shown in FIG. 2. Spindle block 4 has an aperture 8 for receiving the shaft or shank of a vertebral anchor "B" (FIG. 4). Housing or spindle block 4 also has an aperture 9 for receiving the generally cylindrical projection portion 10 of spindle 2. Aperture 8 is further open at 16 to aperture 9 in a manner that the outer limit or profile of aperture 8 intersects the outer limit or profile of aperture 9. Opening at 16 is this manner allows the shaft of a vertebral anchor "B", residing in aperture 8, to contact the projection portion 10 of spindle 2, residing in aperture 9. Moreover, the intersection of these profiles should be sufficiently large to allow vertebral anchor "B" to force projection portion 10 against the inside wall of aperture 9 when set screw 5 is threaded against vertebral anchor "B". Or, the intersection of these profiles should be sufficiently large to allow projection portion 10 to force vertebral anchor "B" against the inside wall of aperture 8 when a set screw (not shown) is threaded into aperture 9 and against projection portion 10. Tightened in either manner, projection 10 and anchor "B" are clamped between setscrew 5 and the inside wall of apertures 8 or 9, thusly locking vertebral anchor "B" to spindle 2. Which, when spindle 2 is tightened to rod "A", clamps vertebral anchor "B" to rod "A".

An advantage of this invention is that the surgeon may adjust the clamp in six manners. The first adjustment 17 is that the surgeon can locate spindle block 4 anywhere along the shank of vertebral anchor "B". The second adjustment 18 is that the surgeon can locate spindle block 4 in most any angle around vertebral anchor "B". The third adjustment 19 is that the surgeon can locate spindle block 4 anywhere along the length of projection portion 10. The fourth adjustment 20 is that the surgeon can locate spindle block 4 in most any angle around projection portion 10. The fifth adjustment 21 is that the surgeon can locate spindle 2 anywhere along the length of rod "A". The sixth adjustment 22 is that the surgeon can locate spindle 2 in most any angle around rod "A".

One alternative embodiment of this invention would also provide a seventh method adjustment. The practitioner of this invention could also use a connector 23 that will provide for engagement of the spindle to the vertebral anchor where the vertebral anchors are at a variety of angles relative to the vertical when the patient is lying down.

Figure 6:
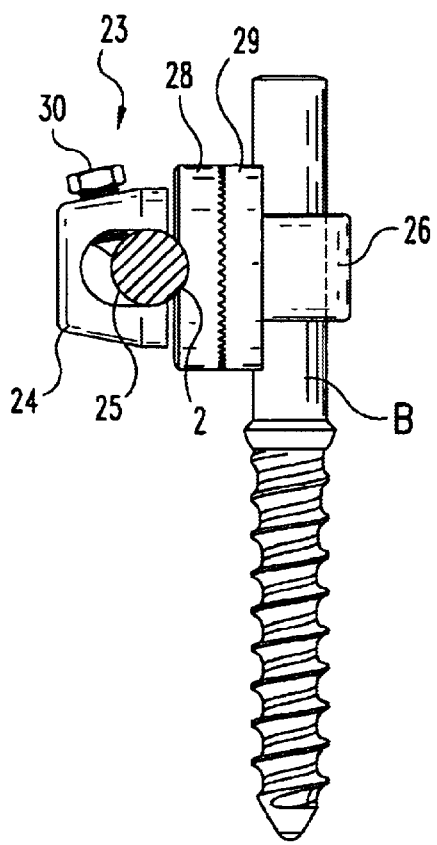
FIGS. 6 and 7 are perspective views of one means for connecting a vertebral anchor to the spindle at a variable angle.
Figure 7:
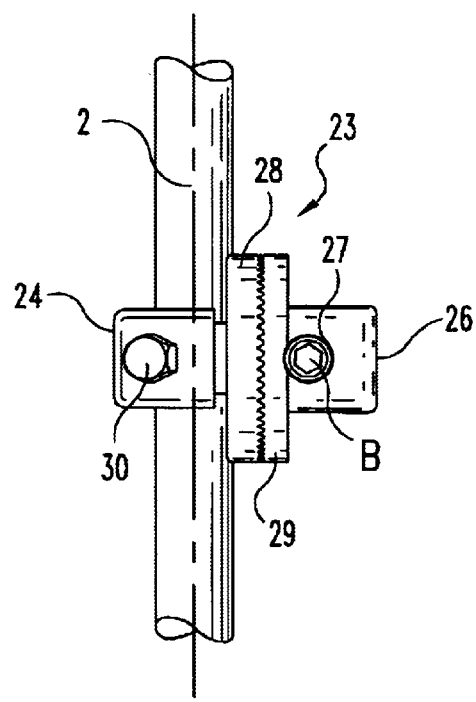

A first example of such a connector 23 is shown in FIGS. 6 and 7. Connector 23 includes a rod or spindle connecting member 24 having an aperture 25 for receiving a portion of the rod or spindle 2 and a bolt connecting member 26 having an aperture 27 for receiving a portion of the bolt or vertebral anchor. The rod or spindle connecting member and bolt connecting member are rotatably engaged to one another. A rod or spindle interface washer 28 is positioned over a portion of the rod connecting member, and a bolt interface washer 29 is positioned over a portion of the bolt connecting member 26. The rod interface washer and bolt interface washer are moveable in part between the rod connecting member and the bolt connecting member, the rod connecting member being fixed against rotation relative to the rod connecting member and the bolt connecting member being fixed against rotation relative to the bolt interface washer. Structure 30 extendable into at least one of the apertures is provided, so as to urge one of the rod and bolt toward the other, and to cause the washers to be pressed together between the rod and the bolt, preventing rotation of the rod interface washer and rod connecting member relative to the bolt interface washer and the bolt connecting member, and securing the spindle to the bolt.

Additional details of this connector can be found in U.S. Pat. Nos. 5,643,263 and 5,885,285 to Simonson, the disclosures of which being specifically incorporated into this specification by reference. One version of this connector is commercially available under the trademark TSRH-3D™ from Medtronic Sofamor Danek, which is located in Memphis, Tenn. U.S.A.

Figure 8:
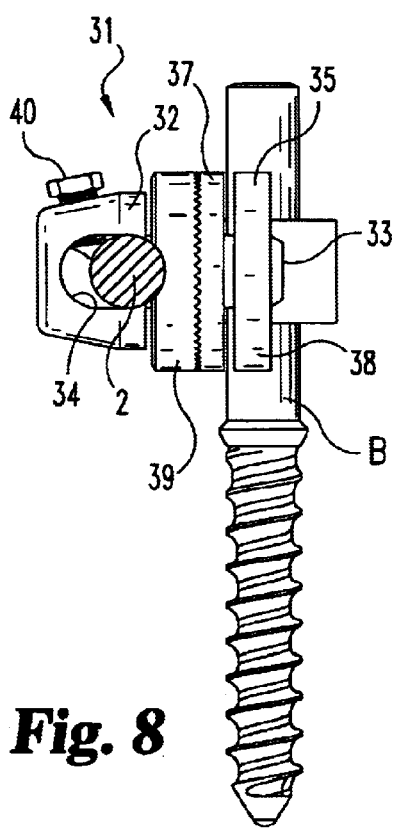
FIGS. 8 and 9 are perspective views of another means for connecting a vertebral anchor to the spindle at a variable angle.
Figure 9:
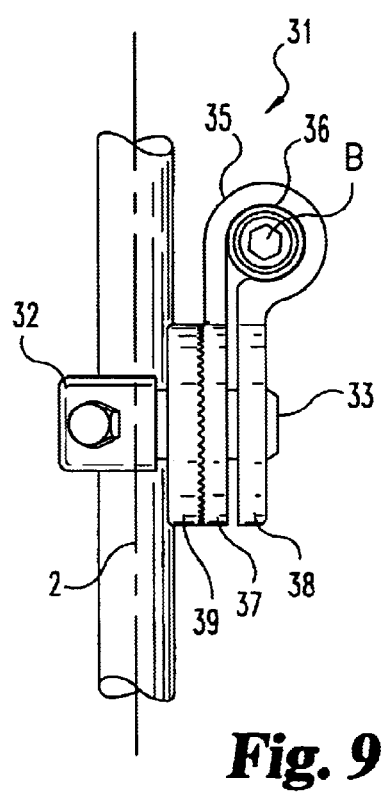

A second example of such a connector 31 is shown in FIGS. 8 and 9. Connector 31 has a bolt 32 with a stop 33 disposed near one end of the bolt and an aperture 34 for receiving a portion of the spindle at the other end. The assembly also has a clevis 35. The clevis defines a bore 36 to hold a portion of the vertebral anchor and the ears of the clevis 37 and 38 have holes through which the bolt 32 is located with the ears positioned between the stop and aperture of the bolt. The assembly also has a rod or spindle interface washer 39 positioned over a portion of the bolt, between the aperture of the bolt and the inside ear 37 of the clevis 35. The rod interface washer is partly movable between the aperture of the bolt and the clevis, but the washer is fixed against rotating in relation to the bolt. Finally, the assembly also includes a screw 40 that threads into the side of the bolt and continues into the aperture 34 of the bolt. The screw is used to push the rod toward the vertebral anchor so that the inside and outside ears of said clevis are pressed together and the clevis is tightened to the vertebral anchor.

Additional details of this connector can be found in U.S. patent application Ser. No. 09/526,104 to Morrison, the disclosure of which is specifically incorporated into this specification by reference.

Figure 12:
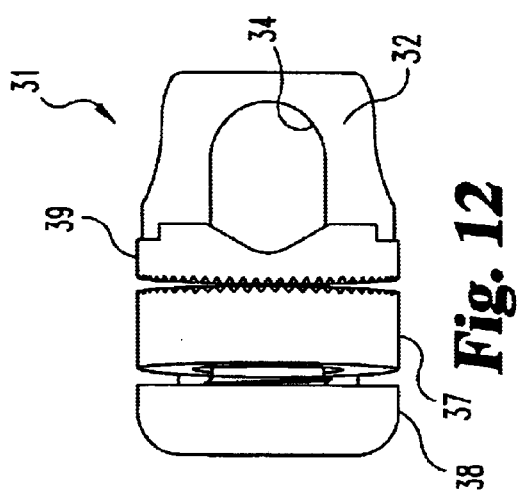
FIGS. 10, 11, and 12 are perspective views of yet another means for connecting a vertebral anchor to the spindle at a variable angle.
Figure 11:
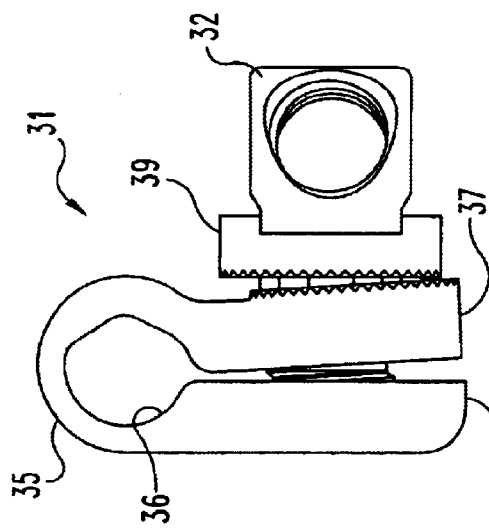
Figure 10:
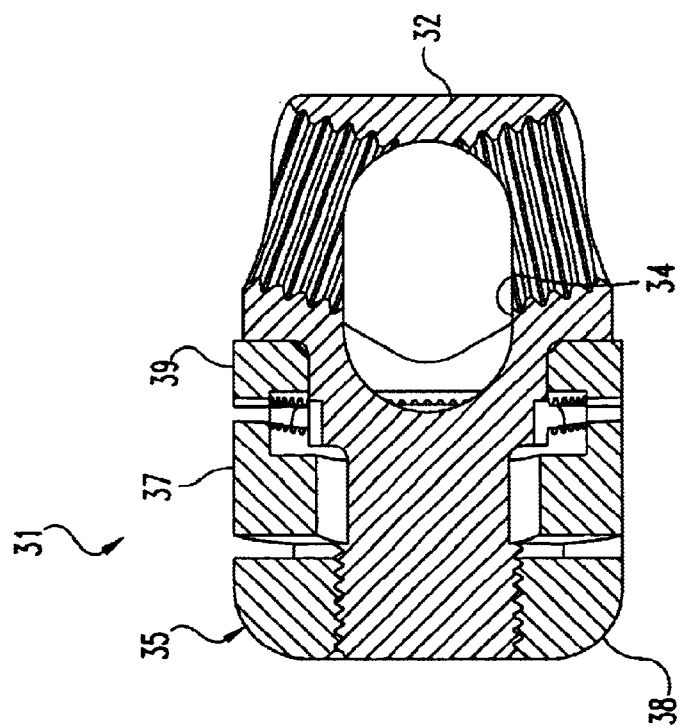

An alternative embodiment of connector 31 is shown in FIGS. 10 to 12. Instead of using stop 33, bolt 32 is rotably attached or threaded directly into ear 38. Attached in this manner, stop 33 is no longer necessary.

While the invention has been illustrated and described in detail, this is to be considered illustrative and not restrictive of the patent rights. The reader should understand that only the preferred embodiments have been presented and all changes and modifications that come within the spirit of the invention are included if the following claims or the legal equivalent of these claims describes them.

What is claimed is:

1. A connection assembly between a spinal implant rod and a vertebral anchor, the assembly comprising:
   (a) a spindle, said spindle having a first aperture with internal walls for receiving a portion of a spinal implant rod;
   (b) a first compression member forceably engageable into said spindle to urge a spinal implant rod against the internal walls of the first aperture;
   (c) a housing, said housing having a second aperture for receiving a portion of said spindle and a third aperture for receiving a portion of the vertebral anchor; and
   (d) a second compression member forceably engageable into housing to urge the spindle against the vertebral anchor, whereby the spindle and the vertebral anchor will be pressed together, securing the housing to the vertebral anchor and the spindle;
   wherein said housing is translatable along the portion of the vertebral anchor.

2. The connection assembly of claim 1, wherein said spindle has a projection portion with a surface, a length and a constant diameter over said length.

3. The connection assembly of claim 2, wherein the projection portion is hollow.

4. The connection assembly of claim 2, wherein the surface of the projection portion contains parallel ridges.

5. The connection assembly of claim 1, wherein the first aperture of said spindle has internal ridges.

6. The connection assembly of claim 1, wherein the second aperture of said housing has internal ridges.

7. The connection assembly of claim 1, wherein the third aperture of said housing has internal ridges.

8. The connection assembly of claim 1 wherein the vertebral anchor includes a generally smooth shaft, and a said spindle block is translatable along the shaft of the vertebral anchor and securable to the shaft at one of a plurality of positions along the shaft.

9. The connection assembly of claim 1 wherein the vertebral anchor includes a shaft having an axis, and said spindle block is rotatable about the axis of the shaft of the vertebral anchor.

10. The connection assembly of claim 1 wherein said spindle includes a projection having a length, said projection being receivable within the second aperture, said spindle block being securable to said projection at a plurality of positions along the length.

11. The connection assembly of claim 1 wherein said spindle block includes a first member securable to said spindle and a second member securable to the vertebral anchor, said members having mutually engageable and interlocking male protrusions and female cavities adapted and configured to fix the angular orientation of said spindle relative to the vertebral anchor at one of a plurality of angular positions.

12. A connection assembly between a spinal implant rod and a vertebral anchor, the assembly comprising:

(a) a spindle, said spindle having a first aperture with internal walls for receiving a portion of a spinal implant rod, said spindle including a projection having an axis and a portion with a cylindrical outer surface;

(b) a first compression member forceably engageable into said spindle to urge a spinal implant rod against the internal walls of the first aperture;

(c) a housing, said housing having a second aperture with walls for receiving a portion of said spindle and a third aperture with walls for receiving a portion of the vertebral anchor, wherein the walls of the second aperture define a first cylinder and the walls of the third aperture define a second cylinder, the walls of the second aperture coacting with the portion of said projection and the walls of the third aperture coacting with the outer surface of the vertebral anchor to establish a substantially fixed angular relationship between the axis of said projection and the vertebral anchor; and (d) a second compression member forceably engageable into housing to urge the spindle against the vertebral anchor, whereby the spindle and the vertebral anchor will be pressed together, securing the housing to the vertebral anchor and the spindle.

13. The connection assembly of claim 12, wherein said spindle has a projection portion with a surface, a length, and a constant diameter over said length.

14. The connection assembly of claim 13, wherein the projection portion is hollow.

15. The connection assembly of claim 13, wherein the surface of the projection portion contains parallel ridges.

16. The connection assembly of claim 12, wherein the first aperture of said spindle has internal ridges.

17. The connection assembly of claim 12, wherein the second aperture of said housing has internal ridges.

18. The connection assembly of claim 12, wherein the third aperture of said housing has internal ridges.

19. The connection assembly of claim 12 wherein said spindle block is translatable along the portion of the vertebral anchor.

20. The connection assembly of claim 12 wherein said spindle block is rotatable about the vertebral anchor.

21. The connection assembly of claim 12 wherein said spindle includes a portion receivable within the second aperture, said spindle block being securable to said spindle at a plurality of positions.

22. The connection assembly of claim 12 wherein said spindle block includes a first member securable to said spindle and a second member securable to the vertebral anchor, said members having interlocking features adapted and configured to fix said spindle relative to the vertebral anchor at one of a plurality of angular positions.

23. A connection assembly between a spinal implant rod and a vertebral anchor, the assembly comprising:

a spindle, said spindle having a first aperture with internal walls for receiving a portion of a spinal implant rod, said spindle including a projection having a length;

a first compression member forceably engageable into said spindle to urge a spinal implant rod against the internal walls of the first aperture;

a housing, said housing having a second aperture for receiving a portion of the projection of said spindle and a third aperture for receiving a portion of the vertebral anchor; and a second compression member forceably engageable into housing to urge the spindle against the vertebral anchor, whereby the spindle and the vertebral anchor will be pressed together, securing the housing to the vertebral anchor and the spindle, said housing being securable to the projection at a plurality of positions along the length.

24. The connection assembly of claim 23, wherein said spindle has a hollow projection portion with a surface, a length and a constant diameter over said length.

25. The connection assembly of claim 23, wherein the surface of the projection portion contains parallel ridges.

26. The connection assembly of claim 23, wherein the first aperture of said spindle has internal ridges, the second aperture of said housing has internal ridges, and the third aperture of said housing has internal ridges.

27. The connection assembly of claim 23 wherein said connecting means is rotatable about the axis of the shaft of the vertebral anchor.

28. The connection assembly of claim 23 wherein said connecting means includes a first member securable to said spindle and a second member securable to the vertebral anchor, said members having mutually engageable and interlocking male protrusions and female cavities adapted and configured to fix the angular orientation of said spindle relative to the vertebral anchor at one of a plurality of angular positions.

* * * * *